United States Patent [19]

Robertson

[11] Patent Number: 4,804,375
[45] Date of Patent: Feb. 14, 1989

[54] ILEOSTOMY VALVE HAVING A ROTATABLE SHUT OFF

[75] Inventor: William G. Robertson, Santa Barbara, Calif.

[73] Assignee: Santa Barbara Medical Foundation Clinic, Santa Barbara, Calif.

[21] Appl. No.: 47,193

[22] Filed: May 6, 1987

[51] Int. Cl.$^4$ .............................................. A61M 1/00
[52] U.S. Cl. ........................................ 604/323; 251/4; 604/335; 600/31
[58] Field of Search ..................... 604/323, 335, 350; 251/4, 9; 128/1 R

[56] References Cited

U.S. PATENT DOCUMENTS

| 2,416,391 | 2/1947 | Hixson | 251/4 |
| 3,371,906 | 3/1968 | Lubold | 251/4 |
| 4,344,434 | 8/1982 | Robertson | 604/335 |
| 4,634,421 | 1/1987 | Hegemann | 604/335 |

FOREIGN PATENT DOCUMENTS

| 16321 | 8/1908 | United Kingdom | 251/4 |

*Primary Examiner*—C. Fred Rosenbaum
*Assistant Examiner*—J. L. Kruter
*Attorney, Agent, or Firm*—Daniel J. Meaney, Jr.

[57] ABSTRACT

An ileostomy valve comprising an attachment plate having a central opening passing therethrough which communicates with a support housing is shown. The support housing has an elongated central member which defines a passageway which communicates with the opening in the attachment plate and which terminates at the remote end of the elongated second member. A cover plate has a central drainage opening extending therethrough. The cover plate is positioned contiguous the attachment plate positioning the coacting member to engage and coact with the attachment plate. An elongated flexible tubing member extends through the central drainage opening in the covering plate, through the opening in the attachment plate, through the passageway in the elongated central member to the second opening in the elongated central member. The other end of the tubing member is affixed to the remote end of the elongated central member defining an unobstructed drainage passageway extending through the elongated central member to the cover plate. When the cover plate is rotated in a selected direction at least 360 degrees relative to the attachment plate, the coacting member coacts with the attachment plate twisting the tubing member to obstruct and close the same to define an obstructed drainage passageway or selectively rotating the cover plate at least 360 degrees, or the same number of degrees used to twist the elongated flexible tubing member to close the same, in a direction opposite to the selected direction to open the drainage passageway.

17 Claims, 3 Drawing Sheets

ILEOSTOMY VALVE HAVING A ROTATABLE SHUT OFF

FIELD OF THE INVENTION

This invention relates to a ileostomy valve which is adapted for use with an ileostomy device and more particularly to an ileostomy valve which is integral with an ileostomy drainage appliance to be worn by a user in order to provide a continent ileostomy which can be easily drained through the ileostomy valve.

BACKGROUND OF THE INVENTION

The use of appliances for occluding colostomies and ileostomies in order to make the same continent is well known in the art. One such ileostomy appliance is disclosed in U.S. Pat. No. 4,344,434, the inventor of which is the same of this invention. A flap valve is used in the interior of an elongated housing member, and the flap valve is opened by inserting a drainage tube is used to drain the appliance.

It is also known in the art for closure appliances to include a plate member and permanent magnets in order to provide a fluid-tight magnetically coupled closure device for intestinal openings. Typical of such devices are those disclosed in U.S. Pat. Nos. 3,952,726; 4,205,678; 4,338,937; and 4,210,132.

A wide variety of mechanical closures, threaded closures and plugs used in ileostomy appliances to close the same and provide fluid-tight seals are disclosed in U.S. Pat. Nos. 4,241,735; 4,217,664; 4,119,100; 3,828,782; 3,802,418; 3,253,594; 2,586,940; 2,561,399; 2,243,529 and 1,810,466.

An artifical sphincter having an attachment plate, which cooperates with a cover having a central aperture for receiving a drainage tube inserted into the appliance through the central opening, is disclosed in U.S. Pat. No. 4,209,010.

A continent ostomy valve having an elongated flexible drainage tube which extends external to the device and wherein the elongated flexible drainage tube is folded and unfolded to open and close the ostomy device is offered for sale and sold by Johnson & Johnson under the Trademark NUVAL continent ostomy valve.

An ileostomy valve which utilizes a folded elongated tubing, the end of which is secured when the same is folded, as a valve for controlling bowel continence is disclosed in U.S. Pat. No. 4,381,765.

SUMMARY OF THE INVENTION

This invention relates to a new and novel ileostomy value adapted to be used with an ileostomy appliance to provide continence and a means for controlling continence. The ileostomy valve comprises an attachment plate having first and second opposed parallel surfaces and an elongated central opening passing therethrough. The first opposed parallel surface includes a groove which is adapted to cooperate with a raised rib to form a threaded surface having at least 360 degree of rotation. The second opposed parallel surface is relatively smooth to facilitate placing the same against the body of a user. A support housing has an elongated central member having a predetermined axial length, and the elongated central member communicates with the attachment plate. The support housing has an aperture extending axially therethrough forming a passageway which terminates in a first opening which communicates with the opening in the attachment plate and a second opening which terminates at the remote end of the elongated second member. A cover plate has a first and second opposed surfaces and a central drainage opening extending therethrough. The first opposed surface is the outer surface of the cover plate and the second opposed surface thereof includes a raised rib adapted to be slideable within the groove formed in the attachment plate. The cover plate is positioned with its second opposed contiguous the first surface of the attachment plate positioning the raised rib to engage with and be slideable within the groove formed on the first opposed surface of the attachment plate. An elongated flexible tubing member has a first end and second end with the first end thereof operatively attached to the driving member receiving section on the first opposed surface of the cover plate. The elongated flexible tubing member extends through the drainage opening in the covering plate, through the opening in the attachment plate, through the passageway in the elongated central member to the second opening in passageway of the elongated central member. The second end of the tubing member is operatively affixed thereto defining an unobstructed drainage passageway extending from the second end of the passageway of the elongated central member to the first surface of said cover plate. When the cover plate is rotated in a selected direction at least 360 degrees relative to the attachment plate, the raised rib slides within the groove twisting the elongated flexible tubing member to obstruct and close the same to define an obstructed drainage passageway which can be selectively opened by rotating the cover plate relative to the attachment plate at least 360 degrees, or the same number of degrees that the elongated flexible tubing member was rotated closing the same in a direction opposite to the selected direction.

The ileostomy appliance disclosed in U.S. Pat. No. 4,344,434, relies on a flap valve which as a closure means. A flap valve does not provide a positive closure, and fluid may unexpectedly bypass the flap valve and drain through the drainage opening in the appliance.

In the known prior art closure appliances having plate members and permanent magnets for forming a magnetically coupled closure device for intestinal opening such as the appliances disclosed in U.S. Pat. Nos. 3,952,726; 4,205,678; 4,338,937; and 4,210,132, the sealing of the appliance depends on the integrity of the fluid tight seal between the cover member and magnets. If the seal is not fluid-tight, or if the magnetic force of the magnets are weaken, of it the cover member is inadvertently jarred or hit, the cover member could easily separate from the device resulting in an unexpected and undesirable drainage of fluid from the appliance.

Mechanical closures, threaded closures and plugs used in ileostomy appliances disclosed in U.S. Pat. Nos. 4,241,735; 4,217,664; 4,119,100; 3,828,782; 3,802,418; 3,253,594; 2,586,940; 2,561,399; 2,243,529 and 1,810,466 are not easily removeable to accommodate fast, easy and efficient drainage of the appliance, which feature are highly desirable for patient self-care device.

The artifical sphincter having an attachment plate which cooperates with a cover having a central aperture for receiving a drainage tube which is inserted into the appliance through the central opening disclosed in U.S. Pat. No. 4,209,010, relies on elongated tubes sliding with each other for drainage purposes, thereby making patient self-care using such drainage devices very clumsy and difficult.

The continent ostomy valve having an elongated flexible drainage tube, a portion of which extends external to the device and wherein folding of the tubing is used to open and close the ostomy device, such as that offered for sale and sold by Johnson & Johnson under the Trademark NUVAL continent ostomy valve and the similar device disclosed in U.S. Pat. No. 4,381,765, each rely on a folded elongated tubing as a valve for controlling bowel continence. The elongated tubing extends external to the appliance, and the actual fold in the elongated tubing is used as the valve. The end of the elongated tubing is secured, when the same is in a folded position, to insure integrity of the seal. As a result, if the end of the tubing inadvertently of accidentally slips out of or is knocked out of the means securing the same, the valve opens, and an unexpected and undesirable discharge of fluid may be experienced. Also, the continual folding and unfolding of the elongated tubing could eventually stress the same, possibly resulting in the appliance leaking, which is undesirable.

The present invention provides a novel and unique ileostomy valve which includes a novel sealing member that overcomes the disadvantages of the prior art devices. The ileostomy valve of the present invention proves a positive seal internal to the appliance, and a valve which a patient can easily use in a self-care program.

Another advantage of the present invention is that the appliance can easily opened and drained through a drainage tube device which is inserted into the appliance to unlock the seal and drain the fluid from the body of a user.

Another advantage of the present invention is that the cover plate can be secured to the attachment plate insuring a positive lock on the seal to prevent inadvertent and unexpected opening of and inadvertent drainage of fluid from the body.

Another advantage of the present invention is that the cover plate can be threaded onto the attachment plate such that the valve can be secured, in a closed position, by rotating the cover plate relative to the attachment plate in a first selected direction 360° or more, and the valve can be opened and in a drainage position by rotating the cover plate relative to the attachment plate in a second selected direction the same number of degrees of rotation used to close the valve.

Another advantage of the present invention is that the elongated flexible tubing member, which functions as the valve, applies an axial compliance loading force between the cover plate and the attachment plate holding the same in mating position independent of whether the valve is either in the closed position or the open position.

Another advantage of the present invention is that a drainage tube device can be used as the means to rotate the cover plate relative to the attachment plate such that a positive pressure is applied therebetween to rotate the elongated flexible tubing member the number of degrees of rotation as necessary to open and close the same. In addition, when the drainage tube device is used to rotate the cover plate relative to the attachment plate, untwisting the tubing member, the drainage tube device, while in place, functions as an inlet or orifice for the fluid drained from the body of a user for disposal into a toilet, collection bag or the like.

Another advantage of the present invention is that the a mechanical lock, such as a locking pin, spring-loaded clamp, clip or raised locking boss can be used to mechanically hold the cover plate relative to the attachment plate to resist any tendency of the cover plate to rotate around its axis relative to the attachment plate din response to a torsional force or torsional spring response due to the twisted elongated flexible tubing member developing a reactive torsion due to being twisted which is reacted to the cover plate and attachment plate. The reacted torsional force is in a direction to rotate the cover plate relative to the attachment plate around the longitudinal axis thereof which would tend to open the secured valve when the same is in a closed position.

Another advantage of the present invention is that the elongated flexible tubing member valve disclosed herein has application as an in-line, rotatable closure or valve for a slurry or semi-solid material flow, e.g. semi-solid fectal matter discharge and the like. The in-line valve can be adapted for use in a material dispensing applications for semi-liquid and semi-solid where valving of fluid is required.

DESCRIPTION OF THE DRAWINGS

These and other advantages of the invention will be readily apparent when considered in light of the detailed description hereinafter of the preferred embodiment and when considered in light of the drawing set forth herein which includes the following Figures.

DESCRIPTION OF THE PREFERRED EMBODIMENT

Figure 1:
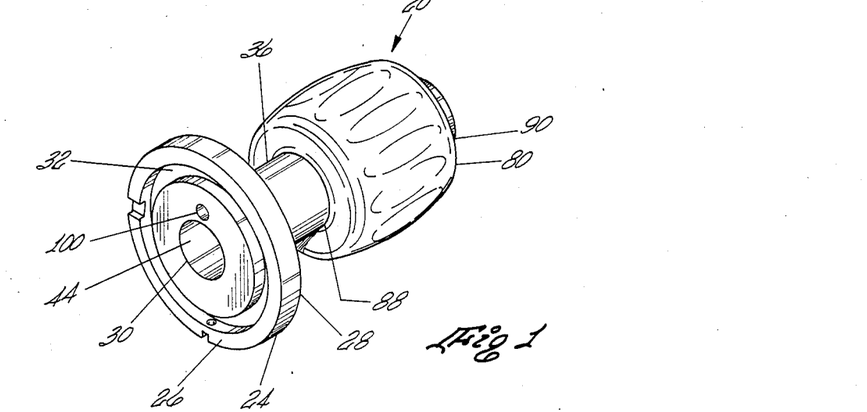
FIG. 1 is perspective view of an ileostomy appliance of the present invention.
Figure 2:
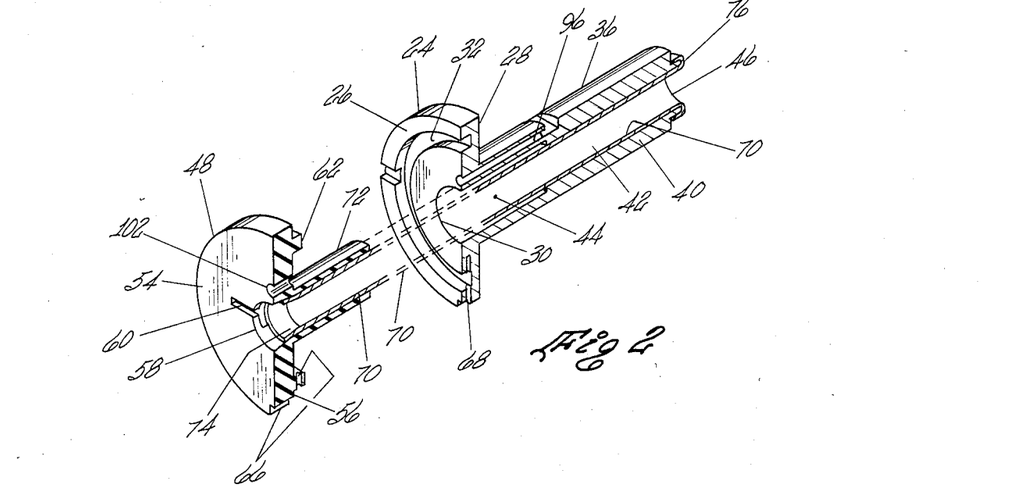
FIG. 2 is an exploded, isometric view, partially in cross-section, of the support housing showing the relationship between the passageway and fluid tube located within the interior of the elongated central member and having a collar portion of the cover plate shown in phantom.

FIG. 1 shows that the ileostomy valve, shown generally by arrow 20, having an attachment plate 24 having first and second opposed parallel surfaces 26 and 28, respectively, and including means defining a central drainage opening 30 passing therethrough defining a continuous, recessed groove 32 which is adapted to cooperate with a raised rib, shown as raised rib 62 in FIG. 2, to form a threaded surface having at least 360 degree of rotation. The raised rib may be rotated within the continuous, recessed groove more than one revolution, e.g., two revolutions would twist the elongated flexible tubing member 720'. The second opposed parallel surface 28 is relatively smooth to enable the same to be urged against the body of a user.

A support housing 36 has an elongated central member 40, shown in FIG. 2, which has a predetermined axial length, and which communicates with the attachment plate 24. The support housing 36 has an aperture extending axially therethrough forming a passageway 42 which terminates in a first opening 44 which communicates with the central drainage opening 30 in the attachment plate 24. The passageway 42 has a second opening 46 which terminates at the remote end of the elongated central member 40.

Referring to FIG. 2, a cover plate 48 has a first and second opposed surfaces 54 and 56 and means defining a central drainage opening 58 therethrough which communicates with a thin wall collar 72. The first opposed surface 54 includes means for forming an driving member receiving slot 60 thereon and the second opposing surface 56 thereof include means defining a raised rib 62 adapted to be slideable with the continuous, recessed groove 32 formed in attachment plate 24. The cover plate 48 is positioned with its second opposed surface 56 contiguous the first opposed surface 26 of the attachment plate 20 such that the thin walled collar 72 slideably enters into the elongated central member positioning the raised rib 62 to engage with and be slideable within the continuous, recessed groove 32 formed on the first opposed surface 26 of the attachment plate 24.

Figures 16, 18:
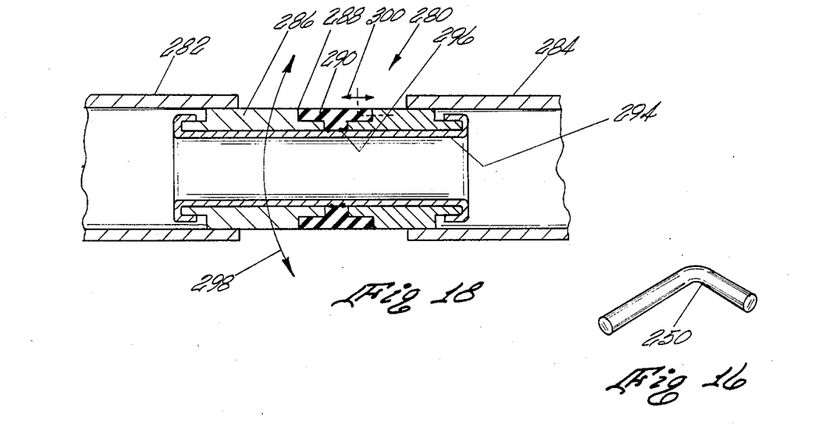
FIG. 16 is a pictorial representation of a locking pin in the form of an "L" shaped member which is inserted into a locking pin slots illustrated in FIG. 2.
FIG. 18 is a pictorial representation, partially in cross-section, showing the use of the teachings of the present invention in an in-line valve application in a continuous tubing path.

The cover plate 48 also includes means for defining a locking pin slot 66 which has a portion thereof formed in the periphery of the cover plate 48, and another portion thereof extending through the raised rib 62 to accommodate an "L" shaped locking pin 250 illustrated in FIG. 16.

A mating locking pin receiving slot 68 is formed in the first opposing surface 26, or top surface, of the attachment plate 24 such that when the raised rib 62 is in the continuous, recessed groove 32, and the same is rotated either 360°, or preferably 720°, therein, the locking pin receiving slots 66 and 68 will be in alignment permitting the locking pin 250, of FIG. 16, to be inserted therein to mechanically lock the same together and override the torsional force applied between the cover plate 48 and the attachment plate 24. The torsional force is applied around the elongated axis of the cover plate 48 and the attachment plate 24 due to the twisting of the elongated flexible tubing member 70. The torsional restoring force applied to the cover plate 48 and the attachment plate 24 is in a direction to force the rotation therebetween to be in a direction causing the valve to open. This is explained in greater detail in connection with the description of FIGS. 17A, 17B and 17C hereinbelow.

The elongated flexible tubing member 70 has a first end 74 and second end 76. In the preferred embodiment, the elongated flexible tubing member 70 may selected to be formed of a non-biodegradable tubing of medical grade Silastic brand flexible tubing, silicon rubber or latex material.

Figure 3:
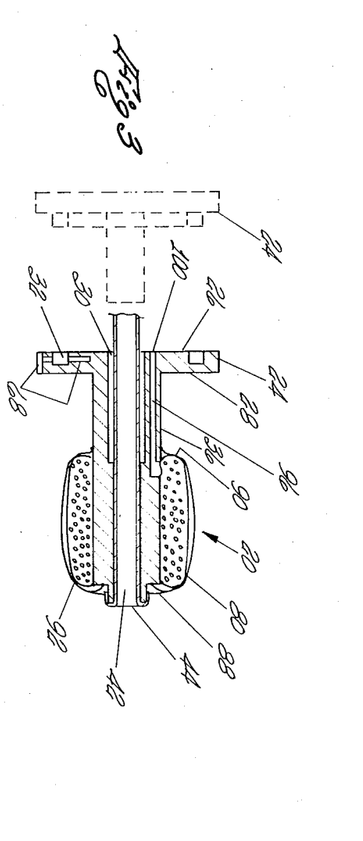
FIG. 3 is a sectional view of the ileostomy appliance showing the detail structure for attachment of the ends of the elongated flexible tubing member to the elongated central member and to the edge of the central drainage opening formed in the covering plate.

Referring to FIGS. 2 and 3, the first end 74 of elongated flexible tubing member 70 is operatively attached to the driving member receiving slot 60 section on the first opposing surface 26 of the cover plate 48 with a flush mounting and adhesive termination described hereinbelow in connection with FIGS. 11 and 14. The second end 76 of elongated flexible tubing member 70 is operatively attached to the second end 46 of the passageway 42 in the elongated central member 40 by means of a wrap-around and adhesive termination described hereinbelow in connection with FIG. 12. The cover plate 48 is shown in phantom and would receive and support the first end 75 end of elongated flexible tubing member 70.

The elongated flexible tubing member 70 extends through the central drainage opening 58 in the covering plate 48, through the central drainage opening 30 in the attachment plate 24, through the passageway 42 in the elongated central member 48 to the second opening 46 of the passageway 42 in the elongated central member 48. The second end 74 of the elongated flexible tubing member 70 is operatively affixed to the elongated central member 48 defining an unobstructed drainage passageway extending from the second end 46 of the passageway 42 in the elongated central member 40 to the first opposing surface 54 surface of the cover plate 48.

In operation, the cover plate 48, when rotated in a selected direction, for example counterclockwise, at least 360 degrees, or more and and preferably 720°, relative to the attachment plate 24, causes the raised rib 62 to slide within the continuous, recessed groove 32, the elongated flexible tubing member is twisted to obstruct and close the same to define an obstructed drainage passageway which can be selectively opened by rotating the cover plate 48 relative to the the attachment plate 24 the same number of degrees of rotation used to twist the elongated flexible tubing member 70, but in a direction opposite used to close the same, e.g. counterclockwise to close, and clockwise to open.

In the ileostomy appliance of the preferred embodiment as illustrated in FIGS. 1 and 3, a preshaped collapsible member 80 is provided as a means to implant the appliance in the user, as is explained in detail in U.S. Pat. No. 4,344,434. The preshaped collapsible member 80 has a fluid tight, outer surface 82, two ends 88 and 90, and an interior cavity 92. The preshaped collapsible member 80 is positioned around the elongated central member 40 with the ends 88 and 90 of the preshaped, collapsible member 80 in fluid tight sealing engagement with the exterior outer surface of the elongated central member 40. One end 88 of the preshaped collapsible member 80 is spaced a predetermined distance from the end of the elongated central member 40 adjacent the attachment plate 24 and the other end 90 of the preshaped collapsible member 80 is adjacent the second opening 44 in the passageway 42 of the elongated central member 40.

The elongated central member 40 includes means, such as closed fluid channel 96, which communicates with a fluid passage opening 100 in attachment plate 24 and fluid passage opening 102 in the cover plate 48. The fluid passage opening 102, the fluid passage opening 100 and the closed fluid channel 96 as used a means for withdrawing fluid from the interior cavity of said preshaped collapsible member 80, an a syringe is normally used for this purpose. The plunger of the syringe is withdrawn to create a reduced pressure therein enabling ambient atmosphere pressure to reduce the geometrical dimension thereof. The plunger of the syringe is depressed for enabling fluid to be drawn into the interior cavity 92 of a deflated preshaped collapsible member 80 at ambient pressure to expand the preshaped collapsible member 80 back to its original shape.

In the preferred embodiment as illustrated in FIG. 3 hereof, a resilient foam material 98, such as non-biodegradable material which could be polyurethane, is positioned within the interior cavity 92 of the preshaped collapsible member 80. The resilient foam material 98 is responsive to the fluid, such as air or gas, being withdrawn therefrom by collapsing with the preshaped collapsible member 80 and is responsive to fluid being drawn into the interior cavity 92 of a deflated preshaped collapsible member to urge the same and the resilient foam material 98 back to their original shape.

It is envisioned that any known means for implanting an ileostomy appliance, or other similar appliance, into the body of a user may incorporate the ileostomy valve disclosed herein. For example, the ileostomy appliances disclosed in U.S. Pat. Nos. 4,381,756 and 3,802,418, as well modifications of the the appliance disclosed in U.S. Pat. No. 4,344,434, could be modified in accordance with the teachings herein to use the ileostomy valve disclosed herein.

Figure 4:
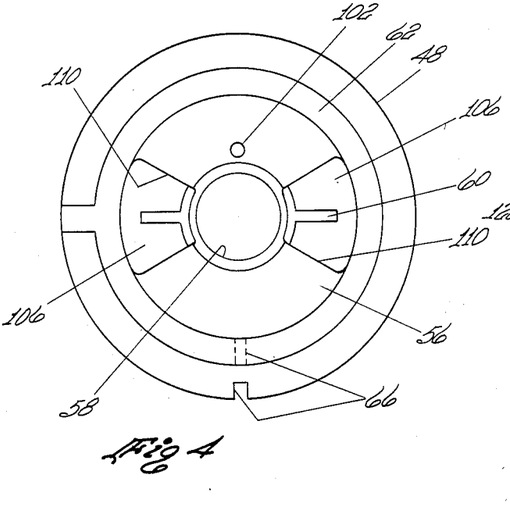
FIG. 4 is a top plan view of the bottom surface of the cover plate which is adapted to mate with the top surface of the attachment plate in the preferred embodiment of the present invention.
Figure 15:
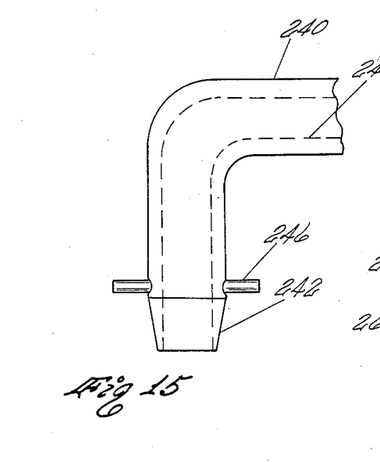
FIG. 15 is a partial pictorial representation, showing a drainage tube device having driving members which cooperate with a cover plate having driving members receiving slots illustrated in FIGS. 2 and 14.

Referring now to FIG. 4, the structure of the cover plate 48 is shown in greater detail. The second opposed surface 56, or bottom surface, shows the central drainage opening 58 and fluid passage opening 102 which passes fluid to the closed fluid channel 96 as described are adapted to receive the driving members 246 formed on the drainage tube device 240 as illustrated in FIG. 15.

In operation, the device members 246 are passed through the driving member receiving slots 60 and into opposed, recessed areas 106 formed in the second opposed surface 56, or bottom surface, of the cover member 48. The recessed areas 106 are triangular shaped to permit the driving members 246, when the drainage tube device 240 is inserted into the cover plate 48, to be shifted away from the receiving slots 60 such that the inserted drainage tube device can be pulled against the bottom of the cover plate 48 to slightly pull the cover plate 48 away from the attachment plate 24. When the drainage tube device is rotated to open or close the elongated flexible tubing member 70, the driving members 246 engage the edges 110 and exert a rotational force against the cover plate 48 rotating the same relative to attachment plate 48. This results in the raised boss 62 sliding in the continuous, recessed groove 32 to either twist or untwist the elongated flexible tubing member 70, depending on whether the ileostomy valve is to be opened or closed.

Figure 5:
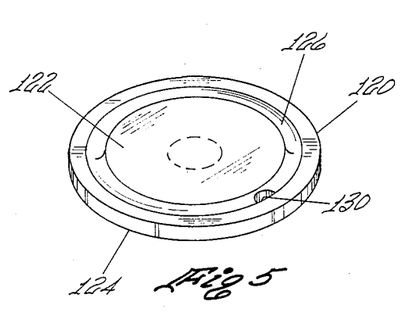
FIG. 5 is a top view of the top surface of the attachment plate having a slot and raised boss opening adapted to mate with the bottom surface of the cover plate having a raised boss in an alternative embodiment of the present invention.

FIG. 5 shows pictorially an alternate embodiment of an attachment plate 120 having a first opposed surface 122, the top surface, and a second opposed surface 124, the bottom surface. The central drainage opening and fluid passage opening would be formed in the attachment plate 120, as well as the driving member receiving slots, to accommodate the desired embodiment of the appliance. A recessed, continuous groove 126 is formed in the first opposed surface 122 and a raised boss receiving aperture 130 is formed within the recessed, continuous groove 126. A raised boss, located on the first opposing surface, or top surface of a mating cover plate, communicates with the raised boss receiving aperture 130.

In this embodiment, in order to disengage the cover plate having the raised boss from the attachment plate 120 of FIG. 4, the cover plate must be slightly raised to lift the raised boss from the raised boss receiving aperture 130. Thus, the structure of the cover plate would include recessed areas similar to recessed area 106 of FIG. 4 to accommodate a drainage tube device having driving members.

The embodiment shown in FIG. 5 results in a positive, tight seal, and mechanically retards any torsional forces from the twisted elongated flexible tubing 70.

Figures 6, 7:
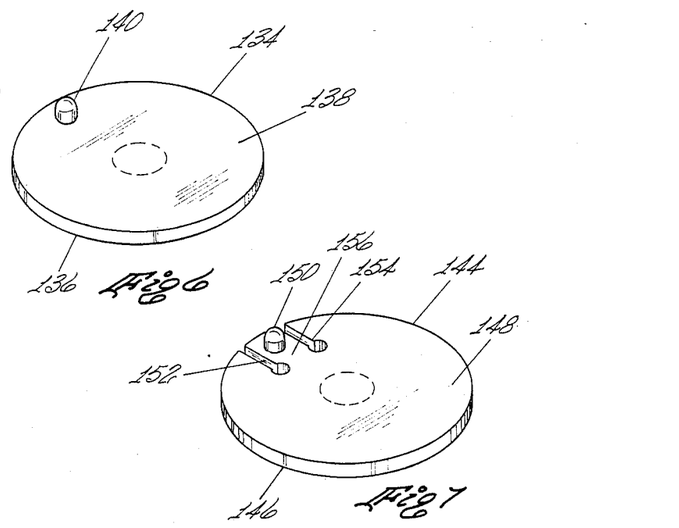
FIG. 6 is a top plan view of the bottom surface of a cover plate having a raised boss which is adapted to mate with the top surface of an attachment plate having a recessed, continuous groove and raised boss receiving aperture in an alternative embodiment of the present invention.
FIG. 7 is a top plan view of the bottom surface of the cover plate having a raised boss located on a spring-loaded tounge forming a cantilever support which is adapted to resiliently mate the raised locking boss with the top surface of an attachment plate having a recessed, continuous groove and raised boss receiving aperture in an alternative embodiment of the present invention.

FIGS. 6 and 7 show two possible embodiment for a cover plate having a raised boss which could be used in combination with the attachment plate 120 of FIG. 5. In FIG. 6, the cover plate 134 has a first opposed surface 136, the top surface, and a second opposed surface 138, the bottom surface. The second opposed surface 138, or bottom surface, has a raised boss 140 located at an appropriate place thereon such that when the cover plate 134 is brought into mating relationship with the top surface 122 of the attachment plate 120 of FIG. 5, the raised boss 140 will engage and slide within the recessed, continuous groove 126 as the cover plate 134 is rotated relative to the attachment plate 120. When the elongated flexible tubing member 70 has been twisted an selected number of degrees of rotation or turns, such as two turns of 360° each, on each 360° of rotation the raised boss 140 drops into and is urged into the raised boss receiving aperture 130 by the resilient or clamping action of the elongated flexible tubing member 70 occurring along the elongated axis thereof due to the elasticity thereof.

FIG. 7 illustrates an alternate embodiment of a cover plate 144 has a first opposed surface 146, the top surface, and a second opposed surface 148, the bottom surface. The second opposed surface 148, or bottom surface, has a raised boss 150 located at an appropriate place thereon. However, in this embodiment, two slits 152 and 154, are formed in the sector of the cover member 144 adjacent the raised boss 150 to form a tounge 156, which functions as a cantilever beam, to resiliently support the raised boss 150.

Thus, when the cover plate 144 is brought into mating relationship with the top surface 122 of the attachment plate 120 of FIG. 5, the raised boss 140 will resiliently slide within the recessed, continuous groove 126 as the cover plate 144 is rotated relative to the attachment plate 120 and when the raised boss 150 is in alignment with the raised boss receiving aperture 130, which occurs when the elongated flexible tubing member has been twisted one turn of 360°, the raised boss 150 is snapped into the raised boss receiving aperture 130 by the spring action of the tounge 156. The raised boss 150 is held in the raised boss receiving aperture 130 by both the spring action of tounge 156 and by the resilient or clamping action of the elongated flexible tubing member 70 along the elongated axis thereof due to the elasticity thereof.

Figure 8:
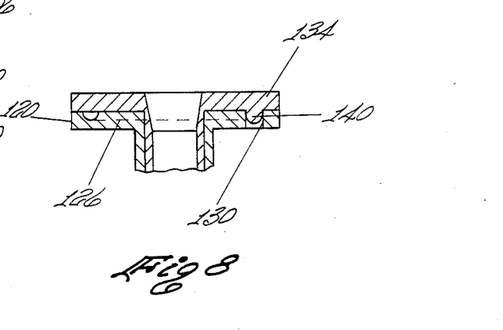
FIG. 8 is a partial pictorial representation, in cross-section, showing the mating relationship an attachment plate shown in FIG. 5 with a cover plate shown in FIG. 6.

FIG. 8 shows the cover plate 134 in mating relationship with the attachment plate 120 which directs the raised boss 140, formed in the bottom surface of the coverplate 134, into the raised boss receiving aperture 130 located in groove 126. As stated hereinbefore, the cover plate 144 of FIG. 7 could be used in mating relationship with the attachment plate 120 of FIG. 5.

Figure 9:
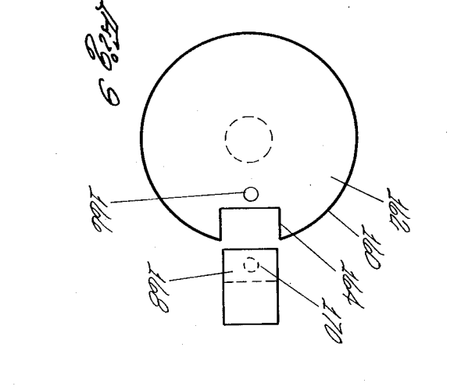
FIG. 9 is a top plan view of a cover plate having a recessed slot and dimple receiving opening for cooperating with a spring-loaded clamp having a dimple which mechanically locks the cover plate to the attachment plate, when the elongated flexible tubing member is twisted developing a torsional restoring force, to mechanically lock the same together to restrain the torsion force applied thereto from the elongated flexible tubing member.

FIG. 9 illustrates yet another embodiment of a cover plate 160 having a top opposed surface, or top surface 162 which has wide slot or recessed slot 164 and a dimple receiving opening 166, both of which are adapted to cooperate with a spring-loaded clamp or clip 168. The spring-loaded clamp 168 includes a dimple 170 which is adapted to mate with dimple receiving opening 166 when the spring-loaded clamp 168 is placed in the recessed slot 164. A similar structure is formed on the bottom surface of a mating attachment plate.

Figure 10:
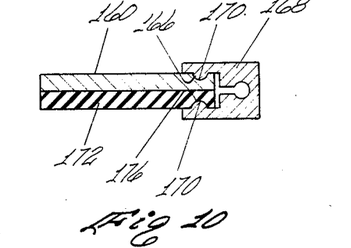
FIG. 10 is a partial pictorial representation, in cross-section, of the cover plate of FIG. 9 and a mating attachment plate having the mechanical spring-loaded clamp attached thereto.

FIG. 10 illustrates the structure of the cover plate 160, an attachment plate 172, having a dimple receiving opening 176 formed therein and a recessed slot, is shown having the cover plate 160 mounted thereon. The spring-loaded clamp or clip 168 mechanically holds the cover plate 160 and the attachment plate 172 together to insure that the twisted elongated flexible tubing member 70 remains twisted maintaining the valve in a secured or closed position.

Figure 11:
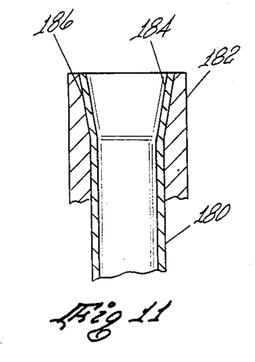
FIG. 11 is a partial pictorial representation, showing flush mounting with an adhesive of the end of the elongated flexible tubing member, which communicates with the central drainage opening in the cover plate, to the interior of the elongated central member.

FIG. 11 illustrates the flush attachment and adhesive method for affixing the elongated flexible tubing member 180 in a cover plate, or at the end of the passageway in the elongated central member. The structure of a cover plate or passageway end is represented pictorially by wall 182. The elongated flexible tubing member 180 has an end 184 which is smooth and of uniform thickness. If the elongated flexible tubing member 180 is cut from a tubing, the end is first prepared for mounting by removing all particles therefrom such that the surface is clean. The exterior of end 184 of elongated flexible tubing member 180 is then treated with an adhesive 186, such as for example a medical grade silicon adhesive. The end 184 is inserted into opening and urged against the wall 182 until the adhesive 186 is cured.

Figure 12:
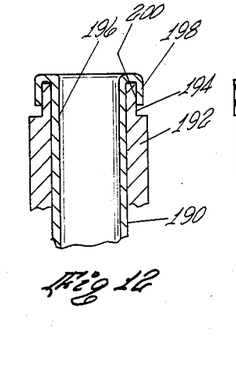
FIG. 12 is a partial pictorial representation, showing a wrap-around mounting with an adhesive on the end of the elongated flexible tubing member, which communicates with the central drainage opening in the cover plate, to the interior of the elongated central member.

FIG. 12 illustrates the wrap-around attachment and adhesive method for affixing the elongated flexible tubing member 190 in a cover plate, or at the end of the passageway in the elongated central member. The structure of a cover plate or passageway end is represented pictorially by wall 192. The wall 192 is machined reducing the diameter thereof to form a recessed area or lip 194 having a thickness which is slightly greater than the thickness of the elongated flexible tubing member 190. The end of the recessed area 194 is then radiused to form a smooth support over which the elongated flexible tubing member 190 can be passed as shown if FIG. 12. The elongated flexible tubing member 190 has an end 196 which is smooth and of uniform thickness. If the elongated flexible tubing member 190 is cut from a tubing, the end is first prepared for mounting by removing all particles therefrom such that the surface is clean. The end 194 is then pulled through the opening defined by wall 192 such that the end 196 has the edge 198 thereof deflected over the recessed lip 194 to position the outer surface of edge 198 in contact with the surface defining the recessed area 198. The exterior edge 198 is treated with an adhesive 200, such as for example a medical grade silicon adhesive, and the edge is urged against the recessed area 198 until the adhesive is cured.

Figures 13, 14:
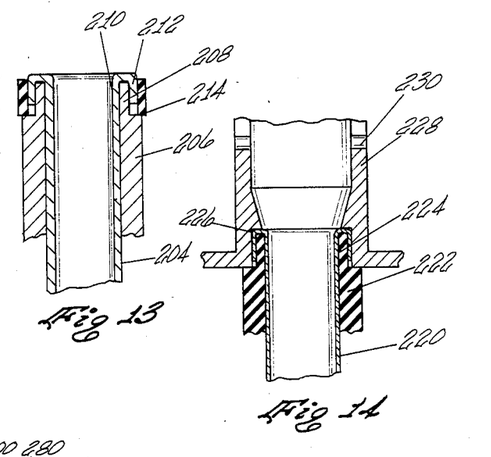
FIG. 13 is a partial pictorial representation, showing a wrap-around mounting with a clamping member on the end of the elongated flexible tubing member, which communicates with the central drainage opening in the cover plate, to the interior of the elongated central member.
FIG. 14 is a partial pictorial representation, showing a wrap-around mounting with an adhesive on the end of the elongated flexible tubing member, which communicates with the central drainage opening in the cover plate having drainage tube device driving pin receiving slots, to the interior of the elongated central member.

FIG. 13 illustrates the wrap-around attachment and clamp method for affixing the elongated flexible tubing member 204 in a cover plate, or at the end of the passageway in the elongated central member. The structure of a cover plate or passageway end is represented pictorially by wall 206. The wall 206 is machined reducing the diameter thereof to form a recessed area or lip 208 having a thickness which is slightly greater than the thickness of the elongated flexible tubing member 204. The end of the recessed area 208 is then radiused to form a smooth support over which the elongated flexible tubing member 204 can be passed as shown in FIG. 13. The elongated flexible tubing member 204 has an end 210 which is smooth and of uniform thickness. If the elongated flexible tubing member 204 is cut from a tubing, the end is first prepared for mounting by removing all particles therefrom such that the surface is clean. The end 210 is then pulled through the opening defined by wall 206 such that the end 210 has the edge 212 thereof deflected over the recessed lip 208 such that the outer surface of edge 212 is in contact with the surface defining the recessed lip 208. The exterior edge 212 is clamped with an appropriate clamp 214 resulting in the edge 212 being mechanically clamped to the recessed lip 208.

The assembly shown in FIG. 14 is adapted to be used for affixing the elongated flexible tubing member 220 to a cover plate having a structure which is similar to that of FIG. 12 for receiving and cooperating with a drainage tube device having driving members extending therefrom. The wall 222 has a raised lip 224 which performs a dual function, namely: (i) to support the end 226 of the elongated flexible tubing member 220; and (ii) forming a mechanical junction with the cover member 228 having the driving member receiving slots 230. The end 226 of the elongated flexible tubing member 220 is mechanically bonded to the recessed lip 224 by an adhesive as discussed in connection with FIG. 12.

FIG. 15 illustrates one embodiment of a drainage tube device 240 having an inlet or orifice 242 which is passed through the central drainage opening, such as central drainage opening 58 in cover plate 48 of FIGS. 1 and 4. A passageway 244 extends from the inlet 242 through the interior of the drainage tube device 240 to a discharge outlet (not shown). The inlet or orifice 242 has driving members 246, in the form of driving pins, extending in opposite directions from the drainage tube device 240. When the inlet or orifice 242 of the drainage tub device 24 is inserted into the central drainage opening 58 of cover plate 48 of FIG. 2, the driving members 264 pass through the driving member receiving slots 60 permitting the driving members 246 to be transported into the recessed area 106 of the cover plate 48 shown in FIG. 4.

FIG. 16 illustrates an "L" shaped locking pin 250 which is adapted to be inserted into slots 66 and 68 of the cover plate 48 and the attachment plate 24 of FIG. 2.

Figure 17:
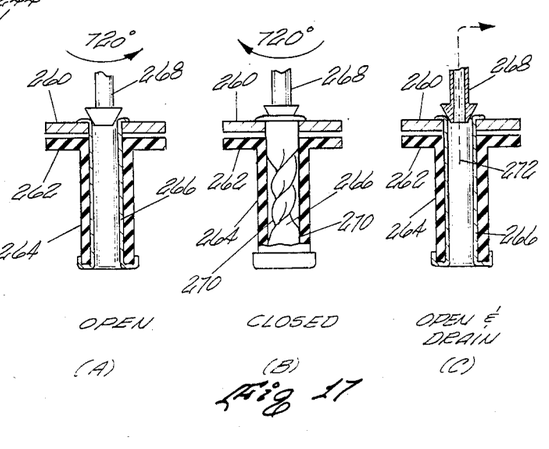
FIGS. 17A, 17B and 17C are pictorial representations of (i) an ileostomy valve elongated flexible tubing member in an open position which is to be rotated 720° counter clockwise by the drainage tube device into a closed position; (ii) an ileostomy valve elongated flexible tubing member in an closed position with the elongated flexible tubing member in a twisted position which secures the valve in the closed position and which is to be rotated 720° clockwise by the drainage tube device into an open drainage position; and (ii) an ileostomy valve elongated flexible tubing member in an open draining position, with the elongated flexible tubing member untwisted, which places the valve in the open drainage position as shown by the arrows thereon depicting drainage of fluid from the body of a user.

FIG. 17A is a pictorial representation of an ileostomy valve having a cover plate 260, attachment plate 262 and an elongated central member 264 and an elongated flexible tubing member 266 operatively attached thereto in a manner as described hereinbefore.

In FIG. 17A, the ileostomy valve is shown in an open position and a drainage tube device 268 is inserted into the cover plate 260 to rotate the same 720° counterclockwise from an open position into a closed position as illustrated in FIG. 17B.

In FIG. 17B, the ileostomy valve is shown in a closed position with the elongated flexible tubing member 266 twisted, as shown by twist 270, which secures the valve in the closed position. In order to open the ileostomy valve to drain fluid, the drainage tube device 268 is inserted into the cover plate 260 and rotates the same 720° clockwise an open drainage position as illustrated in FIG. 17C.

FIG. 17C illustrates an ileostomy valve in an open draining position with the elongated flexible tubing member 266 untwisted which places the valve in the open drainage position to permit fluid flow as shown by direction arrow 272 depicting drainage of fluid from the body of a user.

In the pictorial representation of FIG. 18, an elongated tubing system is shown having an in-line valve 280 installed between the ends 282 and 284 of the tubing system. The in-line valve 280 has a housing support 286 which has a recessed slot 288 which has an annular shaped ring 290 which is rotatable within the recessed slot 288.

An elongated flexible tubing member 294 is affixed to each end of the housing support 286 using an appropriate method of attachment as described hereinabove. The annular shaped ring 290 is attached to the outer surface of the elongated flexible tubing member 294 as shown by adhesive beads 296 using an appropriate adhesive.

Rotation of the the annular shaped ring 290, in either a clockwise or counterclockwise direction, as shown by arrow 298, a selected number of degrees of rotations or turns will twist the elongated flexible tubing member 294 closing the same. Rotating the annular shaped ring 290 in an opposite direction and for the same number of degrees of rotation or turns untwists the elongated flexible tubing member 294 opening the same for passage of fluid through the tubing system.

A slideable locking pin, shown by dashed line 300, is moveable between a locked position and an unlocked position as shown by the arrow and is used to lock the annular support ring 290 relative to the housing support 296 in order to override the torsional force from the twisted tubing 294.

The ileostomy valve disclosed herein has particular utility in the medical field. However, it is envisioned that the concept of controllably twisting an elongated flexible tubing member between between two members each having an end of the elongated flexible tubing member affixed to each member and holding the same together with a clamping force and which applies a torsional force to the same in a direction to open the closed valve, a predetermined number of rotations to open and close a fluid system is novel. Further, a locking means is required to lock the two members in position relative to each other to override the torsion force exerted against the two members when the valve is to be held in a closed position. Removal of the locking means results in the torsional force being applied to the two members in a manner and direction to aid rotation of the two members to untwist the elongated flexible tubing member from the closed position to an open position. Thus, the valve has a hard closing direction which requires more force to close in order to override the resisting torsional force developed by the elongated flexible tubing member as the same is twisted. As a result, two forces are applied to the two member, namely: (i) a clamping force along the elongated axis of the two which pulls the two members together; and (ii) a torsional force which applies a rotational force around the elongated axis of the two members which reacts the twisting force of the elongated flexible tubing member against the two members in a direction which open the valve. As the elongated flexible tubing member is twists tighter, e.g. 720° of rotation relative to 360° of rotation, the magnitude of both the clamping force and rotational torsional force in creases. These forces can be captured to function as a means for clamping the two members together, using a mechanical locking means responsive to the clamping force, to keep the valve closed. When the valve is to be opened, the rotational torsional force can be captured to aid in untwisting the elongated flexible tubing member from the closed position to an open position.

As a result, the fluid valve has an easy open direction, and the valve design could take advantage of the restoring spring force of the twisted elongated flexible tubing member in making a easy and quick opening valve.

It is also envisioned that the torsion spring characteristics of the elongated tubing member could be selected such that the valve has a "snap-open" action in going from a closed position to an open position in response to the torsional force developed from an elongated flexible tubing member having a high number of turns to close the same.

It is also envisioned to be within the teaching of this invention to utilize the clamping force developed between the two members having the elongated flexible tubing member extending therebetween to have the resilient or spring force used as a clamping force holding the two member in intimate relationship through a pin and slot arrangement, or some other appropriate mechanical structure, thereby requiring a positive separation force being applied between the two members, before the same can be rotated relative to each other for opening and/or closing the valve.

What is claimed is:

1. An ileostomy valve comprising
   an attachment plate having first and second opposed parallel surfaces and including means defining a central opening passing therethrough, said first surface including means defining a first coacting means which is adapted to cooperate with a second coacting means to form a coacting surface having at least 360 degree of rotation, said second opposed surface being relatively smooth to enable the same to be urged against the body of a user;
   a support housing having an elongated central member having a predetermined axial length and which communicates with said attachment plate, said support housing having an aperture extending axially therethrough forming a passageway which terminates in a first opening which communicates with said opening in said attachment plate and a second opening which terminates at the remote end of the elongated second member;
   a cover plate having a first and second opposed surface and means defining a central drainage opening therethrough, said first surface including means defining a second coacting means adapted to be coact with the said first coacting means, said cover plate being positioned with its second surface contiguous the first surface of said attachment plate positioning said second coacting means to coact with said first coacting means formed on said first surface of said attachment plate; and
   an elongated flexible tubing member having a first and second end with said first end being operatively attached to said first surface of said cover plate and with said elongated flexible tubing member extending through said drainage opening in said covering plate, through said opening in said attachment plate, through the passageway in said elongated central member to the second opening in passageway of said elongated central member wherein the second end of the passageway of said elongated flexible tubing member is operatively affixed thereto defining an unobstructed drainage passageway extending from the second end of the passageway of said elongated central member to the first surface of said cover plate;
   said cover plate, when rotated in a selected direction at least 360 degrees relative to said attachment plate being operative to coact said first coacting means with said second coacting means to twist said elongated tubing flexible member to obstruct and close the same to define an obstructed drainage passageway which can be selectively opened by rotating said cover plate relative to said attachment plate the same number of degree of rotatation as that used to twist said elongated flexible tubing member and in a direction opposite to said selected direction.

2. The ileostomy valve of claim 1 further wherein said first coacting means is a continuous, recessed groove, and said second coacting means is a raised rib.

3. The ileostomy valve of claim 1 further wherein said cover plate includes a driving member receiving slot located in the vicinity of the opening in said cover plate.

4. The ileostomy valve of claim 1 further comprising
   a preshaped collapsible member having a fluid tight, outer surface, two ends and an interior cavity, said preshaped collapsible member being positioned around said elongated central member with the ends of the preshaped, collapsible in fluid-tight sealing engagement with the exterior outer surface of said elongated member with one end of the preshaped collapsible member being spaced a predetermined distance from the ends of the elongated central member adjacent the attachment plate and the other end of which is adjacent the second opening of the passageway of said elongated central member; and
   means for withdrawing fluid from the interior cavity of said preshaped collapsible member to create a reduced pressure therein enabling ambient atmosphere pressure to reduce the geometrical dimension thereof and for enabling fluid to be drawn into the interior cavity of a deflated preshaped collapsible member at ambient pressure to expand said preshaped collapsible member back to its original shape.

5. The ileostomy valve of claim 4 further comprising a resilient foam material positioned within the interior cavity of said preshaped collapsible member and being responsive to said fluid being withdrawn therefrom by collapsing with said preshaped collapsible member and being responsive to fluid being drawn into the interior cavity of a deflated preshaped collapsible member to urge the same and the resilient foam material back to their original shape.

6. The ileostomy valve of claim 5 wherein said resilient foam material is formed of a non-biodegradable material.

7. The ileostomy valve of claim 6 wherein said resilient foam material is polyurethane.

8. The ileostomy valve of claim 1 further comprising
   a collapsible member having a fluid tight, outer surface, two ends and an interior cavity, said collapsible member being positioned around said elongated central member with the ends thereof in fluid tight sealing engagement with the exterior outer surface of said elongated member with one end of the collapsible member being spaced a predetermined distance from the end of the elongated central member adjacent the attachment plate and the other end of which is adjacent the second opening of the elongated central member; and means for withdrawing fluid from the interior cavity of said collapsible member to create a reduced pressure therein enabling ambient atmosphere pressure to reduce the geometrical dimension thereof and for enabling fluid to be drawn into the interior cavity of a deflated collapsible member at ambient pressure to expand the same back to its original shape.

9. The ileostomy valve of claim 1 wherein said tubing member is formed of a non-biodegradable tubing.

10. The ileostomy valve of claim 9 wherein said tubing member is formed of at least one of a silicon rubber material and a latex material.

11. The ileostomy valve of claim 3 wherein said cover plate includes a recessed area located on the second opposed surface and positioned below said driving member receiving slot, said recessed area including edges which are adapted to engage the driving members to rotate said cover member relative to said attachment plate.

12. The ileostomy valve of claim 2 wherein said attachment plate includes a raised boss receiving aperture located in the continuous, recessed groove for coacting with a raised boss located on the second opposed surface of a mating cover plate.

13. The ileostomy valve of claim 12 wherein the elongated flexible tubing member applies a clamping force along the elongated axis of said cover plate and said attachment plate in mating relationship therewith and a torsional force which is reacted against said cover plate and said attachment plate to rotate the same around the elongated axis thereof in a direction opposite to the selected direction, said cover plate including a raised boss located on the second opposed surface thereof and positioned thereon to coact with the raised boss receiving aperture located in the continuous, recessed groove on said attachment plate to mechanically lock the cover plate and attachment plate together along the elongated axis thereof in response to said clamping force and to retard rotation thereof in response to said torsional force in a direction opposite to said selected direction.

14. The ileostomy valve of claim 13 wherein said cover plate includes a pair of spaced slits on each side of and spaced from said raised boss to form a tongue which resiliently supports said raised boss.

15. A fluid valve for use in a fluid tubing system comprising a first member having first and second opposed surfaces and including means defining a central opening passing therethrough, said first surface including means defining a groove which is adapted to cooperate with a raised rib to form a grooved surface having at least 360 degree of rotation;

a second member having a first and second opposed surfaces and means defining a central opening therethrough, said first surface including means defining a raised rib adapted to be slideable with the said groove, said second member being positioned with its second surface contiguous the first surface of said first member positioning said raised rib to engage with and be slideable within said groove formed on said first surface of said first member; and an elongated flexible tubing member having a first and second end with said first end being operatively attached to said first surface of said second member with said elongated flexible tubing member extending from the second opposed surface of said second member, through said opening in said second member, through said opening in said first member and is operatively affixed to the first opposed surface of said first member defining an unobstructed drainage passageway extending from the second surface of the second member to the first surface of first member;

said first member, when rotated in a selected direction at least 360 degrees relative to said second member being operative to slide said raised rib within groove, to twist said elongated flexible tubing member to obstruct and close the same to define an obstructed passageway which can be selectively opened by rotating said first member relative to said second member the same number of degree of rotation as that used to twist said elongated flexible tubing member and in a direction opposite to said selected direction.

16. The fluid valve of claim 15 wherein the elongated flexible tubing member applies a clamping force along the elongated axis of said first member and said second member in mating relationship therewith and a torsional force which is reacted against said first member and said second member to rotate the same around the elongated axis thereof in a direction opposite to the selected direction, said first and second members including means for mechanically locking the same along the elongated axis thereof in response to said clamping force and to retard rotation thereof in response to said torsional force in a direction opposite to said selected direction.

17. An in-line fluid valve for tubing system comprising a housing support having first and second opposed surfaces and including means defining a central opening passing therethrough, said housing support including means for defining a recessed, annular slot which is adapted to cooperate with a ring member to form a means for rotating the ring member relative to the housing support at least 360 degree of rotation;

an annular shaped ring member having an inner and outer opposed surfaces and means defining a central opening extending therethrough, said ring member including means for rotating said ring member relative to said housing support and around an elongated axis which extends therethrough, said ring member being positioned with its inner surface adjacent the opening in said housing support; and an elongated flexible tubing member having a first end and a second end with said first and second ends being operatively attached to the interior of said housing support in a spaced opposed relationship with said recessed slot intermediate said first and second ends with said elongated flexible tubing member extending through the opening in said housing support, through the interior of said ring member with the exterior surface of elongated flexible tubing member contiguous to and affixed to the inside surface of said ring member so as to rotatable therewith, said ring member being positioned within the recessed slot of said housing support intermediate said first end and second end of said elongated flexible tubing member defining an unobstructed drainage passageway extending through said housing support and ring member;

said ring member, when rotated in a selected direction at least 360 degrees relative to said housing support being operative to twist said elongated flexible tubing member to obstruct and close the same to define an obstructed passageway which can be selectively opened by rotating said ring member relative to said housing member the same number of degree of rotatation as that used to twist said elongated flexible tubing member and in a direction opposite to said selected direction.

* * * * *